United States Patent

Kosley, Jr. et al.

[11] Patent Number: 4,518,713
[45] Date of Patent: May 21, 1985

[54] ANALGESIC SUBSTITUTED-1-AMINOALKYLAMINO-4-ARYLOXYPIPERIDINES

[75] Inventors: Raymond W. Kosley, Jr., Bridgewater; Richard C. Allen, Flemington, both of N.J.

[73] Assignee: Hoechst-Roussel Pharmaceuticals Inc., Somerville, N.J.

[21] Appl. No.: 600,265

[22] Filed: Apr. 13, 1984

[51] Int. Cl.³ ............... A61K 31/445; C07D 211/46
[52] U.S. Cl. .................... 514/326; 514/327; 546/207; 546/221; 549/451
[58] Field of Search .............. 546/207, 221; 514/326, 514/327

[56] References Cited

U.S. PATENT DOCUMENTS 3,743,645  7/1973  Helsley ........................... 546/216
3,869,459  3/1975  Milkowski et al. ............. 544/399

Primary Examiner—Robert T. Bond
Attorney, Agent, or Firm—Tatsuya Ikeda

[57] ABSTRACT

There are described analgesic substituted-1-aminoalkylamino-4-aryloxypiperidines of the formula

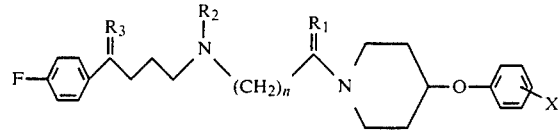

where X is hydrogen, loweralkyl, $CF_3$, acetyl or halogen; n is 1 or 2; $R_1$ is $H_2$ or oxygen; $R_2$ is H, loweralkyl or benzyl; and $R_3$ is oxygen or $-OCH_2CH_2O-$, which are useful as analgesic agents and intermediate compounds therefor.

114 Claims, No Drawings

ANALGESIC SUBSTITUTED-1-AMINOALKYLAMINO-4-ARYLOXYPIPERIDINES

This invention relates to novel substituted-1-aminoalkylamino-4-aryloxypiperidines of the formula

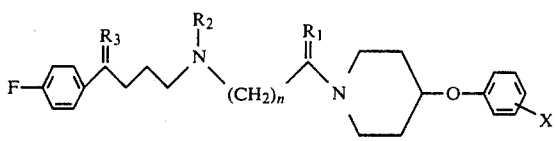

(I)

where X is hydrogen, loweralkyl, $CF_3$, acetyl or halogen; n is 1 or 2; $R_1$ is $H_2$ or oxygen; $R_2$ is H, loweralkyl or benzyl; and $R_3$ is oxygen or $-OCH_2CH_2O-$, which are useful as analgesic agents; to analgesic compositions comprising same; to novel intermediate compounds therefor; and to methods of synthesizing the foregoing compounds.

The novel intermediate compounds of this invention mentioned above are compounds of the Formulas II through V shown below, where $R_4$ is loweralkyl and X is as defined above.

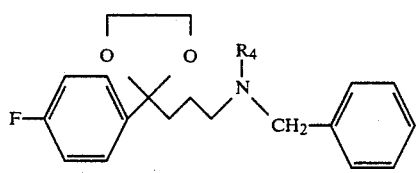

(II)

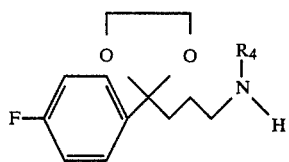

(III)

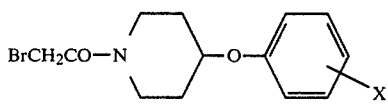

(IV)

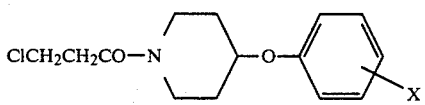

(V)

Needless to say, compounds of Formula I where $R_3$ is $-OCH_2CH_2O-$ can be considered intermediates for synthesizing the corresponding ketone compounds of Formula I where $R_3$ is oxygen, because the ethylene ketal compounds can readily be converted to the corresponding ketone compounds by hydrolysis.

To the best of our knowledge the compounds of the present invention have not heretofore been described or suggested.

In the above definitions and as used throughout the specification and the appended claims the term "lower" means the group it is describing contains 1 to 4 carbon atoms. The term "alkyl" refers to a straight or branched chain hydrocarbon containing no unsaturation e.g. methyl, ethyl, n-propyl, isopropyl, tertiary-butyl, etc. The term "halogen" means fluorine, chlorine, bromine or iodine.

The compounds of the present invention may be prepared by following one or more of the following steps. The groups X, $R_1$, $R_2$, $R_3$ and $R_4$ shall have the same meanings as defined above throughout the specification and the appended claims, unless otherwise specifically stated or indicated.

STEP A

Compound II is prepared by alkylation of a secondary amine of the formula

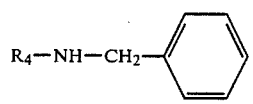

with 2-(3-chloropropyl)-2-(4-fluorophenyl)-1,3-dioxolane having Formula (VI) below.

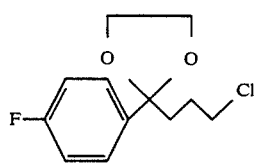

(VI)

Said alkylation is conducted typically in the presence of an acid scavenger such as $K_2CO_3$ in a suitable medium such as dimethylformamide (DMF). A typical reaction condition is stirring at 80°–105° C. for a few hours.

STEP B

Compound III is prepared by hydrogenolysis of Compound II in the presence of hydrogen gas and a catalyst. A suitable example of the catalyst is palladium on carbon and a typical reaction condition is shaking at 40° C. under 50 psi of hydrogen pressure for several hours.

STEP C

Compound IV is prepared by reacting a compound of the formula

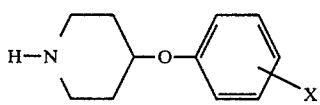

(VII)

with bromoacetyl bromide. Typically the reaction is conducted in the presence of an acid scavenger such as $NaHCO_3$ in a suitable medium such as dichloroethane. A typical reaction condition is stirring at room temperature for a few hours.

STEP D

A compound of the formula

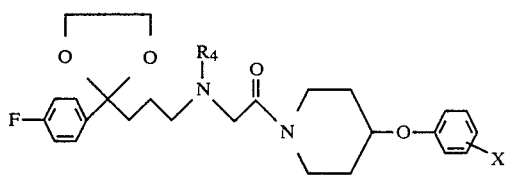
(Ia)

is prepared by alkylation of Compound III with Compound IV. Said alkylation reaction is conducted usually in the presence of an acid scavenger such as $K_2CO_3$ in a suitable medium such as ethanol. A typical reaction condition is stirring at room temperature for 1 hour and at reflux (in ethanol) for 1 hour.

STEP E

A compound of the formula

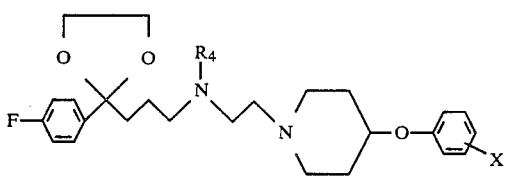
(Ib)

where X is hydrogen, loweralkyl, $CF_3$ or halogen is prepared by reduction of Compound Ia (X being hydrogen, loweralkyl, $CF_3$ is halogen). Usually said reduction is conducted by use of lithium aluminum hydride in a suitable solvent such as anhydrous THF. A typical reaction condition is stirring at reflux (in THF) for 16 hours.

STEP F

A compound of the formula

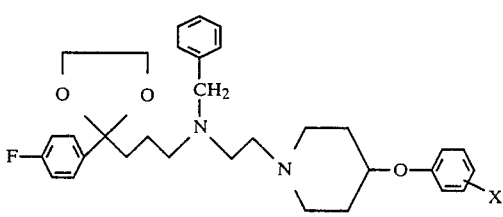
(Ic)

is prepared by alkylation of a secondary amine of the formula

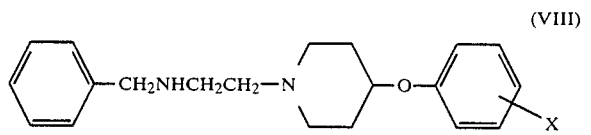
(VIII)

with Compound VI. Usually said alkylation is conducted in the presence of an acid scavenger such as $K_2CO_3$ in a suitable medium such as DMF. A typical reaction condition is stirring at 80°–85° C. for 3 hours and at 100°–105° C. for 2 hours.

STEP G

A compound of the formula

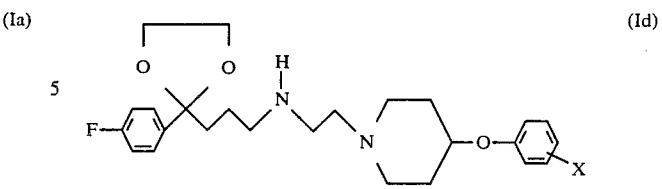
(Id)

is prepared by hydrogenolysis of Compound Ic in the presence of hydrogen gas and a catalyst. Usually said hydrogenolysis is conducted by use of palladium on carbon as a catalyst. A typical reaction condition is shaking at 50° C. under 50 psi of hydrogen pressure for 0.5 hour.

STEP H

A compound of the formula

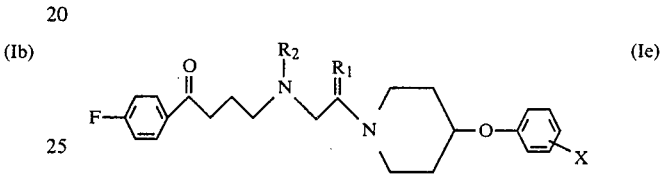
(Ie)

is prepared by hydrolysis of a compound of the formula

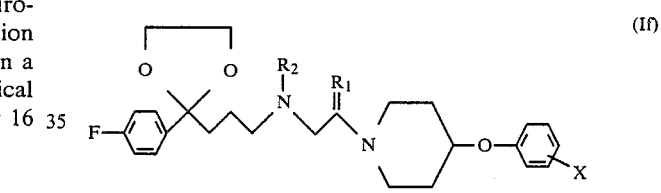
(If)

which is obtained from STEP D, E, F, or G above. Usually said hydrolysis is conducted in the presence of an acid such as hydrogen chloride in a suitable medium such as $H_2O$/methanol. A typical reaction condition is refluxing (in methanol/water) for 3 hours.

STEP I

Compound V is prepared by reacting Compound VIII with beta-chloropropionyl chloride. The reaction is conducted in substantially the same manner as described in STEP C above.

STEP J

A compound of the formula

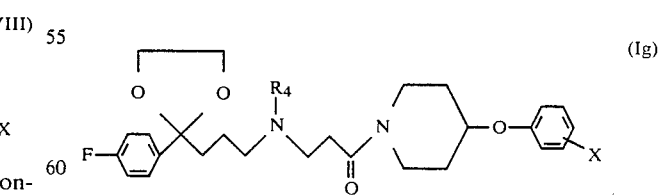
(Ig)

is prepared by alkylation of Compound III with Compound V. The reaction is conducted in substantially the same manner as described in STEP D above.

STEP K

A compound of the formula

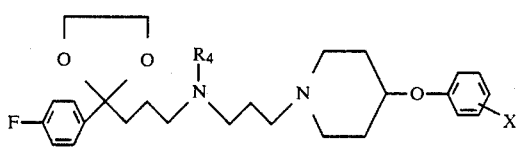

where x is hydrogen, loweralkyl, CF₃ or halogen is prepared by reduction of Compound Ig (X being hydrogen, loweralkyl, CF₃ or halogen). The reduction is conducted in substantially the same manner as described in STEP E above.

STEP L

A compound of the formula

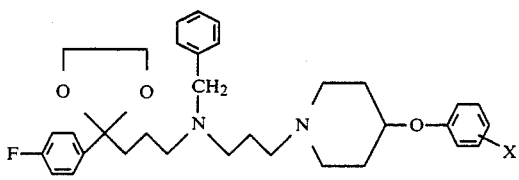

is prepared by alkylation of a secondary amine of the formula

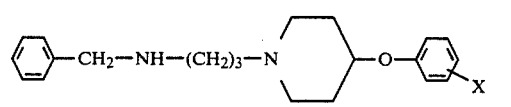

with Compound VI. The alkylation reaction is conducted in substantially the same manner as described in STEP F above.

STEP M

A compound of the formula

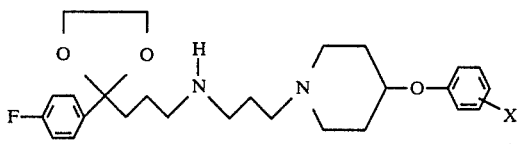

is prepared by hydrogenolysis of Compound Ii in the presence of hydrogen gas and a catalyst. The hydrogenolysis reaction is conducted in substantially the same manner as described in STEP G above.

STEP N

A compound of the formula

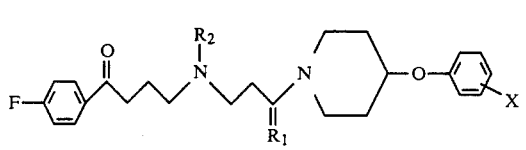

is prepared by hydrolysis of a compound of the formula

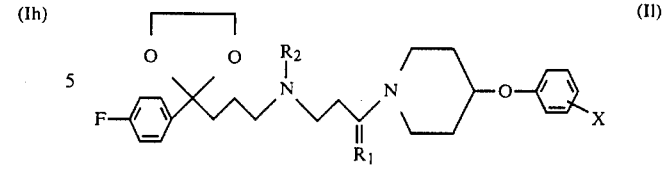

which is obtained from STEP J, K, L or M above. The reaction is conducted in substantially the same manner as described in STEP H above.

STEP O

Compound X having the formula

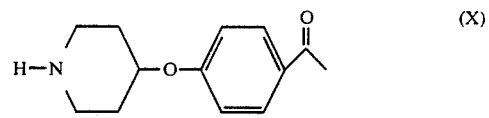

which corresponds to the starting compound VII where X is acetyl may be prepared by reacting 4-hydroxypiperidine with p-fluoroacetophenone in the presence of a suitable base and solvent such as dimsyl anion in DMSO. A typical reaction condition is stirring at room temperature for 16 hours.

STEP P

Compound XI having the formula

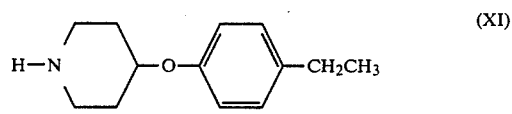

which corresponds to the starting compound VII where X is ethyl may be prepared by reduction of Compound X. Said reduction may be accomplished, for instance, by the Wolff-Kishner method using hydrazine and KOH in a suitable solvent such as triethylene glycol. A typical reaction condition is stirring at 190°–195° C. for several hours.

All other starting materials shown above are either known compounds or easily prepared by routine methods known to the art from readily available materials.

Compounds of Formula I of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table 1 shows a result of the test of the analgesic activities of some of the compounds of this invention.

TABLE 1

| Compounds | ANALGESIC ACTIVITY PQW Dose (mg/kg, s.c.) | % Response |
|---|---|---|
| 1-{N—{3-[2-(4-Fluorophenyl)-1,3-dioxolan-2-yl]propyl}-N—methylaminoacetyl}-4-(4-methylphenoxy)piperidine oxalate | 20 | 68 |
| 1-{2-{N—[4-(4-Fluorophenyl)-4-oxobutyl]-N—methylamino}ethyl}-4-(2-fluorophenoxy)piperidine dihydrochloride | 10 | 50 |
| 1-{2-{N—[4-(4-Fluorophenyl)-4- | 14.4 | 50 |

TABLE 1-continued

ANALGESIC ACTIVITY PQW

| Compounds | Dose (mg/kg, s.c.) | % Response |
|---|---|---|
| oxobutyl]-N—methylamino}ethyl}-4-(4-fluorophenoxy)piperidine dihydrochloride | | |
| 1-{2-{N—{3-[2-(4-Fluorophenyl)-1,3-dioxolan-2-yl]propyl}-N—methylamino acetyl}-4-trifluoromethylphenoxy)piperidine oxalate | 25 | 32 |
| 1-{2-{N—[4-(4-Fluorophenyl)-4-oxobutyl]-N—methylamino}ethyl}-4-(4-trifluoromethylphenoxy)piperidine dihydrochloride | 25 | 54 |
| 1-{3-{N—[4-(4-Fluorophenyl)-4-oxobutyl]-N—methylamino}propyl}-4-(3-chlorophenoxy)piperidine dihydrochloride | 25 | 43 |
| 1-{2-{N—[4-(4-Fluorophenyl)-4-oxobutyl-N—ethylamino}ethyl}-4-(3 chlorophenoxy)piperidine dihydrochloride | 25 | 43 |
| 1-{N—{3-[2-(4-Fluorophenyl)-1,3-dioxolan-2-yl]propyl}-N—methylaminoacetyl}-4-phenoxypiperidine oxalate | 25 | 57 |
| 1-{2-{N—[4-(4-Fluorophenyl)-4-oxobutyl]-N—methylamino}ethyl}-4-phenoxypiperidine dihydrochloride | 7.9 | 50 |
| 1-{N—{3-[2-(4-Fluorophenyl)-1,3-dioxolan-2-yl]propyl}-N—methylaminoacetyl}-4-(3-chlorophenoxy)piperidine oxalate | 25 | 23 |
| 1-{2-{N—[4-(4-Fluorophenyl)-4-oxobutyl]-N—methylamino}ethyl}-4-(3-chlorophenoxy)piperidine dihydrochloride | 13.9 | 50 |

Compounds of the invention compare favorably with the well known analgesic compound ibuprofen, which, in a similar test exhibited an analgesic $ED_{50} = 10.4$ mg/kg, orally.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:

1-{N-{3-[2-(4-Fluorophenyl)-1,3-dioxolan-2-yl]propyl}-N-methylaminoacetyl}-4-(3-chlorophenoxy)piperidine oxalate;

2-(3-[methylamino]propyl)-2-(4-fluorophenyl)-1,3-dioxolane hydrochloride;

1-{2-{N-{3-[2-(4-Fluorophenyl)-1,3-dioxolan-2-yl]propyl}-N-methylamino}ethyl}-4-(3-chlorophenoxy)piperidine dihydrochloride;

1-{2-{N-[4-(4-Fluorophenyl)-4-oxobutyl]-N-methylamino}ethyl}-4-(3-chlorophenoxy)piperidine dihydrochloride;

2-[3-(N-Benzyl-N-methylamino)propyl]-2-(4-fluorophenyl)-1,3-dioxolane hydrochloride;

1-{2-{N-{3-[2-(4Fluorophenyl)-1,3-dioxolan-2-yl]propyl}-N-methylamino}ethyl}-4-phenoxypiperidine dihydrochloride;

1-{2-{N-[4-(4-Fluorophenyl)-4-oxobutyl]-N-methylamino}ethyl}-4-phenoxypiperidine dihydrochloride;

2-[3-(N-Benzyl-N-ethylamino)propyl]-2-(4-fluorophenyl)-1,3-dioxolane hydrochloride;

1-{3-{N-{3-[2-(4-Fluorophenyl)-1,3-dioxolan-2-yl]propyl}-N-methylamino}propyl}-4-(3-chlorophenoxy)piperidine dihydrochloride 2-[3-(Ethylamino)propyl]-2-(4-fluorophenyl)-1,3-dioxolane hydrochloride;

1-{2-{N-{3-[2-(4-Fluorophenyl)-1,3-dioxolan-2-yl]propyl}-N-ethylamino}ethyl}-4-(3-chlorophenoxy)piperidine dihydrochloride;

1-{2-{N-[4-(4-Fluorophenyl)-4-oxobutyl]-N-ethylamino}ethyl}-4-(3-chlorophenoxy)piperidine dihydrochloride;

1-{2-{N-{3-[2-(4-Fluorophenyl)-1,3-dioxolan-2-yl]propyl}-N-methylamino}acetyl}-4-trifluoromethylphenoxy)piperidine oxalate;

1-{3-{N-[4-(4-Fluorophenyl)-4-oxobutyl]-N-methylamino}propyl}-4-(3-chlorophenoxy)piperidine dihydrochloride;

1-{2-{N-{3-[2-(4-Fluorophenyl)-1,3-dioxolan-2-yl]propyl}-N-benzylamino}ethyl}-4-(3-chlorophenoxy)piperidine dioxalate;

1-{2-{N-[4-(4-Fluorophenyl)-4-oxobutyl]-N-methylamino}ethyl}-4-(4-trifluoromethylphenoxy)-piperidine dihydrochloride;

1-{N-{3-[2-(4-Fluorophenyl)-1,3-dioxolan-2-yl]propyl}-N-methylaminoacetyl}-4-phenoxypiperidine oxalate;

1-{2-{N-{3-[2-(4-Fluorophenyl)-1,3-dioxolan-2-yl]propyl}-N-ethylamino}ethyl}-4-(3-chlorophenoxy)piperidine dihydrochloride;

1-{N-{3-[2-(4-Fluorophenyl)-1,3-dioxolan-2-yl]propyl}-N-methylaminoacetyl}-4-(4-fluorophenoxy)piperidine oxalate;

1-{2-{N-{3-[2-(4-Fluorophenyl)-1,3-dioxolan-2-yl]propyl}-N-methylamino}ethyl}-4-(4-fluorophenoxy)piperidine dihydrochloride;

1-{2-{N-[4-(4-Fluorophenyl)-4-oxobutyl]-N-methylamino}ethyl}-4-(4-fluorophenoxy)piperidine dihydrochloride;

1-{N-{3-[2-(4-Fluorophenyl)-1,3-dioxolan-2-yl]propyl}-N-methylaminoacetyl}-4-(2-fluorophenoxy)piperidine oxalate;

1-{2-{N-{3-[(4-Fluorophenyl)-1,3-dioxolan-2-yl]propyl}-N-methylamino}-ethyl}-4-(2-fluorophenoxy)piperidine dihydrochloride;

1-{2-55 N-[4-(4-Fluorophenyl)-4-oxobutyl]-N-methylamino}ethyl}-4-(2-fluorophenoxy)piperidine dihydrochloride;

1-{2-{N-{3-[2-(4-Fluorophenyl)-1,3-dioxolan-2-yl]propyl}-N-methylamino}ethyl}-4-(4-chlorophenoxy)piperidine dihydrochloride;

1-{2-{N-[4-(4-Fluorophenyl)-4-oxobutyl]-N-methylamino}ethyl}-4-(4-chlorophenoxy)piperidine dihydrochloride;

1-{N-{3-[2-(4-Fluorophenyl)-1,3-dioxolan-2-yl]propyl}-N-methylaminoacetyl}-4-(4-chlorophenoxy)piperidine oxalate;

1-{2-55 N-{[3-(4-Fluorophenyl)-1,3-dioxolan-2-yl]propyl}-N-methylamino}ethyl}-4-(4-methylphenoxy)piperidine dihydrochloride;

1-{N-{3-[2-(4-Fluorophenyl)-1,3-dioxolan-2-yl]propyl}-N-methylaminoacetyl}-4-(4-methylphenoxy)piperidine oxalate;

4-(4-Acetylphenoxy)piperidine oxalate;

1-{N-{3-[2-(4-Fluorophenyl)-1,3-dioxolan-2-yl]propyl}-N-methylaminoacetyl}-4-(4-acetylphenoxy)piperidine oxalate; and 1-{N-{3-[2-(4-Fluorophenyl)-1,3-dioxolan-2-yl]propyl}-N-methylaminoacetyl}-4-(4-ethylphenoxy)piperidine oxalate.

The following examples are for illustrative purposes and are not to be considered as limiting the invention disclosed herein. All temperatures are given in degrees Celcius.

EXAMPLE 1

1-{N-{3-[2-(4-Fluorophenyl)-1,3-dioxolan-2-yl]propyl}-N-methylaminoacetyl}-4-(3-chlorophenoxy)piperidine oxalate To a suspension of sodium bicarbonate (34 g, 0.040 mol), 400 ml of methylene chloride and bromoacetyl bromide (15.7 ml, 36.5 g, 0.176 mol) cooled by an ice-/salt bath was added dropwise a solution of 4-m-chlorophenoxypiperidine (34.9 g, 0.165 mol) in 400 ml of methylene chloride. The reaction mixture was stirred 1 hour at 0° and 3 hours at room temperature. The reaction mixture was poured into water, extracted with methylene chloride, and the extract was washed with water, 3N HCl, saturated sodium bicarbonate and saturated sodium chloride. Evaporation of the solvent provided N-(2-bromoacetyl)-4-(m-chlorophenoxy)piperidine.

To a suspension of 2-[3-(methylamino)propyl]-2-(4-fluorophenyl)-1,3-dioxolane (7.2 g, 30.0 mmol), potassium carbonate (10.6 g, 76.8 mmol) and 120 ml of ethanol at 0° was added dropwise a solution of N-(2-bromoacetyl)-4-(3-chlorophenoxy)piperidine (11.3 g, 34.0 mmol) in 120 ml of ethanol. The solution was stirred 1 hour at room temperature and at reflux for 1 hour. The mixture was poured into saturated sodium bicarbonate, extracted with methylene chloride, washed with water and dried over magnesium sulfate. Filtration followed by evaporation of the solvent provided an oil. Yield: 11.0 g of 1-{N-{3-[2-(4-fluorophenyl)-1,3-dioxolan-2-yl]propyl}-N-methylaminoacetyl}-4-(3-chlorophenoxy)piperidine oxalate. Yield from 4-(3-chlorophenoxy)piperidine: 43%; from N-(2-bromoacetyl)-4-(3-chlorophenoxy)-piperidine: 77%.

Analysis: Calculated for $C_{28}H_{34}ClFN_2O_8$: 57.88%C, 5.95%H, 4.82%N. Found: 57.48%C, 6.18%H, 4.46%N.

EXAMPLE 2

2-(3-[Methylamino]propyl)-2-(4-fluorophenyl)-1,3-dioxolane hydrochloride

A suspension of 12 g of 5% palladium on carbon, 135 g (0.369 mol) of 2-[3-(N-benzyl-N-methylamino)-propyl]-2-(4-fluorophenyl)-1,3-dioxolane hydrochloride, 0.1 ml of a saturated solution of hydrogen chloride in methanol and 1 liter of methanol was shaken at 40° for 5 hours under 50 psi hydrogen. The suspension was allowed to cool to room temperature, filtered and the solvent evaporated. Trituration with anhydrous ether, followed by filtration provided 94.6 g (0.343 mol, 93%) of 2-(3-[methylamino]propyl)-2-(4-fluorophenyl)-1,3-dioxolane hydrochloride. Crystallization from isopropyl alcohol provided analytically pure material.

Analysis: Calculated for $C_{13}H_{19}ClFNO_2$: 56.63%C, 6.95%H, 5.08%N. Found: 56.67%C, 7.04%H, 4.94%N.

EXAMPLE 3

1-{2-{-N-[4-(4-Fluorophenyl)-4-oxobutyl]-N-methylamino}ethyl}-4-(3-chlorophenoxy)piperidine dihydrochloride A solution prepared from 8.55 g (15.5 mmol) of 1-{2-{N-{3-[2-(4-fluorophenyl)-1,3-dioxolan-2-yl]propyl}-N-methylamino}ethyl}-4-(3-chlorophenoxy)piperidine dihydrochloride, 130 ml of methanol and 50 ml of 3N HCl was heated at reflux for 3 hours under nitrogen and allowed to cool to room temperature. The methanol was evaporated and the residue made basic with saturated sodium carbonate and extracted with ether. The ether extract was washed with saturated sodium chloride and dried over potassium carbonate. Filtration followed by evaporation of the solvent provided an oil. The yield of the dihydrochloride was 6.8 g (13.4 mmol, 86%). Recrystallization from ethanol/methanol provided analytically pure material.

Analysis: Calculated for $C_{24}H_{32}Cl_3FN_2O_2$: 56.98%C, 6.38%H, 5.54%N. Found: 56.74%C, 6.17%H, 5.36%N.

EXAMPLE 4

2-[3-(N-Benzyl-N-methylamino)propyl]-2-(4-fluorophenyl)-1,3-dioxolane hydrochloride A suspension of 17 g of potassium iodide, 424 g (3.07 mol) of potassium carbonate, 1125 ml of DMF, 150 g (1.23 mol) of benzylmethylamine and 292 g (1.19 mol) of 2-(3-chloropropyl)-2-(4-fluorophenyl)-1,3-dioxolane was heated at 80° for 1 hour and at 90°–105° for 2 hours and allowed to cool to room temperature. The suspension was poured into water, extracted with methylene chloride, washed four times with water and dried over potassium carbonate. Evaporation of the solvent provided an oil. Formation of the hydrochloride was carried out in 20% iPrOH/Et₂O. The yield of the hydrochloride was 274 g (0.749 mol, 62%).

Analysis: Calculated for $C_{20}H_{24}FNO_2;HCl$: 65.65%C, 6.89%H, 3.83%N. Found: 65.35%C, 6.81%H, 3.86%N.

EXAMPLE 5

1-{2-{N-{3-[2-(4-Fluorophenyl)-1,3-dioxolan-2-yl]propyl}-N-methylamino}ethyl}-4-(3-chlorophenoxy)piperidine dihydrochloride To a suspension prepared from 3.00 g (39.5 mmol) of 50% lithium aluminum hydride in oil and 100 ml of dry THF and maintained at 0° was added dropwise a solution of 1-{N-{3-[2-(4-fluorophenyl)-1,3-dioxolan-2-yl]propyl}-N-methylaminoacetyl}-4-(3-chlorophenoxy)piperidine oxalate in 100 ml of dry THF. The mixture was heated at reflux under nitrogen for 12 hours, allowed to cool to room temperature and subsequently cooled in an ice bath. To the mixture was added slowly, dropwise 3 ml of water followed by 3 ml of 15% sodium hydroxide and 9 ml of water. The suspension was filtered and washed with 150 ml of THF, and the THF was evaporated. The residue was extracted with ether, washed with saturated sodium chloride and dried over potassium carbonate. The yield of the dihydrochloride was 9.36 g (79%). Crystallization from ethanol provided analytically pure material.

Analysis: Calculated for $C_{26}H_{36}Cl_3FN_2O_3$: 56.78%C, 6.60%H, 5.10%N. Found: 56.93%C, 6.73%H, 5.24%N.

EXAMPLE 6

1-{2-{N-{3-[2-(4-Fluorophenyl)-1,3-dioxolan-2-yl]propyl}-N-methylamino}ethyl}-4-phenoxypiperidine dihydrochloride A suspension prepared from 2.25 g of 5% palladium on carbon, 400 ml of methanol, 0.2 ml of saturated HCl/methanol and 11.19 g (19.3 mmol) of 1-{N-{3-[2-(4-fluorophenyl)-1,3-dioxolan-2-yl]propyl}-N-methylaminoacetyl}-4-(3-chlorophenoxy)piperidine oxalate was shaken under 50 psi hydrogen at 50° for 4 hours. The mixture was allowed to cool to room temperature and filtered, and the solvent was evaporated to provide an oil. The oil was shaken with saturated sodium carbonate, extracted with ether, dried over potassium carbonate, filtered, and the solvent evaporated to provide 1-{N-{3-[2-(4-fluorophenyl)-1,3-dioxolan-2-yl]propyl}-N-methylaminoacetyl}-4-phenoxypiperidine.

To a suspension of 1.9 g (25.1 mmol) of lithium aluminum hydride (50% in oil; washed three times with hexane) in 75 ml dry THF, cooled by an ice bath, was added dropwise a solution of 1-{N-{3-[2-(4-fluorophenyl)-1,3-dioxolan-2-yl]propyl}-N-methylaminoacetyl}-4-phenoxypiperidine (from above) in 75 ml of dry THF. The suspension was heated at reflux for 12 hours and allowed to cool to room temperature. To the mixture, in an ice bath were added slowly dropwise 1 ml of water, 1 ml of 15% NaOH and 3 ml of water. The mixture was filtered and washed with THF. The solvent was evaporated from the filtrate to provide an oil which was extracted with ether and washed with saturated sodium chloride. The solution was dried over potassium carbonate and filtered to provide an oil. The overall yield of the dihydrochloride was 7.47 g (82.0%).

Analysis: Calculated for $C_{26}H_{35}FN_2O_3.2HCl$: 60.58%C, 7.24%H, 5.44%N. Found: 60.64%C, 7.18%H, 5.47%N.

EXAMPLE 7

1-{2-{N-[4-(4-Fluorophenyl)-4-oxobutyl]-N-methylamino}ethyl}-4-phenoxypiperidine dihydrochloride A solution prepared from 150 of ml methanol, 75 ml of 3N HCl and 6.63 g (12.9 mmol) of 1-{2-{N-3-[2-(4-fluorophenyl)-1,3-dioxolan-2-yl]-propyl-N-methylamino}ethyl}-4-phenoxypiperidine dihydrochloride was heated at reflux for 3 hours under nitrogen and allowed to cool to room temperature. The solution was made basic with saturated sodium carbonate and the methanol evaporated. The mixture was extracted with ether, washed with saturated sodium chloride and dried over potassium carbonate. The yield of the dihydrochloride was 5.89 g (96.9%). Recrystallization from ethanol/methanol provided 3.68 g (60%) of the dihydrochloride.

Analysis: Calculated for $C_{24}H_{31}FN_2O_2.2HCl$: 61.01%C, 7.04%H, 5.93%N. Found: 61.02%C, 7.05%H, 5.76%N.

EXAMPLE 8

2-[3-(N-Benzyl-N-ethylamino)propyl]-2-(4-fluorophenyl)-dioxolane hydrochloride A suspension prepared from 5.0 g of potassium iodide, 127 g of potassium carbonate, 335 ml of DMF, 50 g (0.37 mol) of ethyl benzyl amine and 87.2 g (0.357 mol) of 2-(3-chloropropyl)-2-(4-fluorophenyl)-1,3-dioxolane was heated at 80°–90° for 2.5 hours and at 100°–105° for 1 hour. The mixture was allowed to cool to room temperature, poured into water, extracted with ether, washed four times with water and once with saturated sodium chloride. The solution was dried over potassium carbonate and the solvent evaporated to provide an oil. The yield of the hydrochloride was 86.6 g (0.228 mol, 63%).

Analysis: Calculated for $C_{21}H_{26}FNO_2 \cdot HCl$: 66.40%C, 7.17%H, 3.69%N. Found: 66.10%C, 7.00%H, 3.48%N.

EXAMPLE 9

1-{3-{N-{3-[2-(4-Fluorophenyl)-1,3-dioxolan-2-yl]propyl}-N-methylamino}-propyl}-4-(3-chlorophenoxypiperidine)dihydrochloride To a suspension of 1.0 g (13.2 mmol) of lithium aluminum hydride (50% in oil; washed three times with hexane) in 35 ml dry THF cooled in an ice bath was added dropwise a solution of 1-{3-{N-{3-[2-(4-fluorophenyl)-1,3-dioxolan-2-yl]propyl}-N-methylamino}-1-oxopropyl}-4-(3-chlorophenoxy)piperidine in 35 ml THF. The suspension was heated at reflux under nitrogen for 12 hours and allowed to cool to room temperature. The mixture was cooled in an ice bath. To the mixture was added dropwise 0.5 ml of water, 0.5 ml of 15% NaOH and 1.5 ml of water. The mixture was filtered and the residue washed with THF. Evaporation of the THF provided an oil which was dissolved in ether and washed with water and saturated sodium chloride. The solution was dried over potassium carbonate and the ether evaporated to provide an oil. The yield of the dihydrochloride was 3.06 g (69.8%, 5.43 mmol). Crystallization from ethanol provided 1.14 g (26%) of analytically pure material.

Analysis: Calculated for $C_{27}H_{36}ClFN_2O_3 \cdot 2HCl$: 57.50%C, 6.79%H, 4.97%N. Found: 57.25%C, 6.82%H, 4.79%N.

EXAMPLE 10

2-[3-(Ethylamino)propyl]-2-(4-fluorophenyl)-1,3-dioxolane hydrochloride

A suspension prepared from 47.2 g (0.124 mmol) of 2-[3-(N-benzyl-N-ethylamino)propyl]-2-(4-fluorophenyl)-1,3-dioxolane hydrochloride, 0.035 ml of saturated HCl/methanol, 350 ml of methanol, and 4 g of 5% palladium on carbon was shaken at 50° under 50 psi hydrogen for 5 hours. The mixture was allowed to cool to room temperature and filtered. Evaporation of the solvent followed by trituration with ether provided 34.8 g (96%) of product. Recrystallization from ether/isopropyl alcohol provided analytically pure material.

Analysis: Calculated for $C_{14}H_{20}FNO_2 \cdot HCl$: 58.02%C, 7.31%H, 4.83%N. Found: 57.86%C, 7.62%H, 4.72%N.

EXAMPLE 11

1-{2-{N-{3-[2-(4-Fluorophenyl)-1,3-dioxolan-2-yl]propyl}-N-ethylamino}-ethyl}-4-(3-chlorophenoxy)-piperidine dihydrochloride To a suspension of 0.57 g (8.86 mmol) of lithium aluminum hydride (59% in oil; washed 3 times with hexane) in 20 ml THF (freshly distilled from lithium aluminum hydride) cooled in an ice bath was added dropwise a solution of 2.08 g (4.12 mmol) of 1-{N-{3-[2-(4-fluorophenyl)-1,3-dioxolan-2-yl]propyl}-N-ethylaminoacetyl}-4-(3-chlorophenoxy)piperidine in 20 ml of dry THF. Following the addition, the mixture was heated at reflux under nitrogen for 16 hours and allowed to cool to room temperature. The mixture was cooled in an ice bath. To the mixture were added six drops of water, six drops of 15% NaOH and 1 ml of water. The suspension was filtered and the residue washed with THF. Evaporation of the solvent provided an oil which was shaken with water, extracted with ether, washed with saturated sodium chloride and dried over potassium carbonate. Evaporation of the solvent provided an oil. The product yield as maleate was 1.26 g. Recrystallization provided 0.80 g (34%) of analytically pure material.

Analysis: Calculated for $C_{27}H_{36}ClFN_2O_3 \cdot 2HCl$: 57.50%C, 6.79%H, 4.97%N. Found: 57.84%C, 6.48%H, 5.13%N.

EXAMPLE 12

1-{2-{N-[4-(4-Fluorophenyl)-4-oxobutyl]-N-ethylamino}ethyl}-4-(3-chlorophenoxy)piperidine dihydrochloride A solution of 5.68 g (10.1 mmol) of 1-{2-{N-{3-[2-(4-fluorophenyl)-1,3-dioxolan-2-yl]propyl}-N-ethylamino}ethyl}-4-(3-chlorophenoxy)piperidine dihydrochloride, 150 ml of methanol and 70 ml of 3N HCl was heated at reflux for 4 hours under nitrogen and allowed to cool to room temperature. The mixture was neutralized with saturated sodium bicarbonate after which the methanol was evaporated. The residual aqueous solution was made basic with saturated sodium carbonate, extracted twice with ether and dried over potassium carbonate. Evaporation of the solvent provided an oil. The yield of the dihydrochloride was 5.20 g (99%). Recrystallization from ethanol provided 4.16 g (80%) of analytically pure material.

Analysis: Calculated for $C_{25}H_{32}ClFN_2O_2 \cdot 2HCl$: 57.75%C, 6.59%H, 5.39%N. Found: 57.86%C, 6.56%H, 5.45%N.

EXAMPLE 13

1-{2-{N-{3-[2-(4-Fluorophenyl)-1,3-dioxolan-2-yl]propyl}-N-methylamino}acetyl}-4-trifluoromethylphenoxy)piperidine oxalate To a suspension of 34.6 g (0.250 mol) of potassium carbonate, 2-(3-[methylamino]propyl)-2-(4-fluorophenyl)-1,3-dioxolane (liberated from 23.5 g, 97.9 mmol, of the hydrochloride) and 400 ml of anhydrous ethanol was added dropwise at room temperature over 2 hours a solution of 40.5 g (0.111 mol) of N-(2-bromoacetyl)-4-(4-trifluoromethylphenoxy)piperidine in 400 ml of ethanol. The mixture was stirred at room temperature for 1 hour and at reflux for 1 hour under nitrogen and allowed to cool to room temperature. The mixture was filtered and 75% of the ethanol was evaporated. The residue was dissolved in ether, washed with saturated sodium bicarbonate and the aqueous layer extracted again with ether. The combined organic fractions were washed with saturated sodium chloride and dried over potassium carbonate. Evaporation of the solvent provided an oil (36.1 g). The oil was chromatographed on 600 g of alumina; eluted 3 times using 600 ml ether aliquots. Evaporation of the solvent provided an oil. The yield of the oxalate (recrystallized once from isopropyl alcohol/ethanol) was 14.1 g (23.3%). Recrystallization from ethanol provided analytically pure material.

Analysis: Calculated for $C_{27}H_{32}F_4N_2O_4 \cdot C_2H_2O_4$: 56.67%C, 5.58%H, 4.56%N. Found: 56.47%C, 5.45%H, 4.45%N.

EXAMPLE 14

1-{3-{N-[4-(4-Fluorophenyl)-4-oxobutyl]-N-methylamino}propyl}-4-(3-chlorophenoxy)piperidine dihydrochloride A solution prepared from 3.36 g (5.96 mmol) of 1-{3-{N-{3-[2-(4-fluorophenyl)-1,3-dioxolan-2-yl]propyl}-N-methylamino}propyl}-4-(3-chlorophenoxy)piperidine dihydrochloride, 90 ml of methanol and 40 ml of 3N HCl was heated at reflux under nitrogen for 3 hours. The solution was allowed to cool to room temperature, neutralized with saturated sodium bicarbonate and the methanol evaporated. The residue was made basic with sodium carbonate, extracted twice with ether and washed with saturated sodium chloride. The ether solution was dried over potassium carbonate. Filtration followed by evaporation of the solvent provided an oil. The dihydrochloride was recrystallized from ethanol/methanol to provide 2.50 g (74.4%) of the desired ketone.

Analysis: Calculated for $C_{25}H_{32}ClFN_2O_2 \cdot 2HCl$: 57.75%C, 6.59%H, 5.39%N. Found: 57.56%C, 6.44%H, 5.03%N.

EXAMPLE 15

1-{2-{N-{3-[2-(4-Fluorophenyl)-1,3-dioxolan-2-yl]propyl-N-benzylamino}-ethyl}-4-(3-chlorophenoxy)piperidine dioxalate A suspension prepared from 0.1 g of KI, 1-[2-(N-benzylamino)-ethyl]-4-(3-chlorophenoxy)piperidine (liberated from 1.0 g, 2.34 mmol, of the hydrochloride hemihydrate), 0.81 g (5.86 mmol) of potassium carbonate, 0.61 g (2.49 mmol) of 2-(3-chloropropyl)-2-(4-fluorophenyl)-1,3-dioxolane and 2 ml of DMF was heated at 80°–85° under nitrogen for 3 hours, at 100°–105° for 2 hours and allowed to cool to room temperature. The mixture was poured into water, extracted twice with ether, washed with saturated sodium chloride and dried over potassium carbonate. Filtration followed by evaporation of the solvent provided an oil. The oil was dissolved in diethyl ether, placed on a column containing 60 g of alumina, and eluted twice using 60 ml aliquots of diethyl ether. Evaporation of the solvent provided an oil. The yield of the dioxalate was 0.80 g (46%), m.p. 120°–126°.

Analysis: Calculated for $C_{32}H_{38}ClFN_2O_3 \cdot 2C_2H_2O_4$: 58.97%C, 5.77%H, 3.82%N. Found: 58.92%C, 5.85%H, 3.97%N.

EXAMPLE 16

1-{2-[4-(4-Fluorophenyl)-4-oxobutyl]-N-methylamino}ethyl}-4-(4-trifluoromethylphenoxy)piperidine dihydrochloride To a suspension of 1.12 g of lithium aluminum hydride (59% in oil; washed three times with hexane) in 37 ml of dry THF, cooled in an ice bath, was added dropwise a solution of 1-{N-{3-[2-(4-fluorophenyl)-1,3-dioxolan-2-yl]propyl}-N-methylaminoacetyl}-4-trifluoromethylphenoxy)piperidine in 37 ml of dry THF. The mixture was heated at reflux under nitrogen for 18 hours. The suspension was allowed to cool to room temperature and then cooled in an ice bath. To the mixture were added dropwise, slowly, 0.6 ml of water, 0.6 ml of 15% sodium hydroxide and 1.8 ml of water. The suspension was filtered and the residue washed with 60 ml of THF. The THF was evaporated from the filtrate and the residue was taken up in ether, washed with water and saturated sodium chloride, and dried over potassium carbonate. Filtration followed by evaporation of the solvent provided an oil. Addition of ethereal hydrogen chloride to a solution of the oil in ether provided a white solid (3.81 g). The solid was dissolved in methanol and the solution cooled to provide, after filtration, 0.37 g of 1-methyl-4-(4-trifluoromethylphenoxy)piperidine hydrochloride. The methanol was evaporated from the residue to provide a solid which was recrystallized from acetonitrile to provide 1.34 g (2.28 mmol, 33%) of 1-{2-{N-{3-[2-(4-fluorophenyl)-1,3-dioxolan-2-yl]propyl}-N-methylamino}ethyl}-4-(4-trifluoromethylphenoxy)piperidine dihydrochloride.

A solution of 3.75 g (6.38 mmol) of 1-{2-{N-{3-[2-(4-fluorophenyl)-1,3-dioxolan-2-yl]propyl}-N-methylamino}ethyl}-4-(4-trifluoromethylphenoxy)piperidine dihydrochloride, 55 ml of methanol, and 22.5 ml of 3N HCl was heated at reflux under nitrogen for 3 hours. The reaction mixture was allowed to cool to room temperature and was subsequently neutralized with sodium bicarbonate. The methanol was evaporated and the residue made basic with sodium carbonate. The mixture was extracted with ether, washed with saturated sodium chloride and dried over potassium carbonate. Filtration followed by evaporation of the solvent provided an oil. The dihydrochloride was recrystallized from acetonitrile to provide 1.75 g (50%) of 1-{2-{N-[4-(4-fluorophenyl)-4-oxobutyl]-N-methylamino}ethyl}-4-(4-trifluoromethyl-phenoxy)piperidine dihydrochloride.

Analysis: Calculated for $C_{25}H_{30}F_4N_2O_2 \cdot 2HCl$: 55.66%C, 5.98%H, 5.19%N. Found: 55.59%C, 5.95%H, 5.01%N.

EXAMPLE 17

1-{N-{3-[2-(4-Fluorophenyl)-1,3-dioxolan-2-yl]propyl}-N-methylaminoacetyl}-4-phenoxypiperidine oxalate A suspension of 1.0 g (1.72 mmol) of 1-{N-{3-[2-(4-fluorophenyl)-1,3-dioxolan-2-yl]propyl}-N-methylaminoacetyl}-4-(3-chlorophenoxy)piperidine oxalate, 0.3 g of 5% palladium on carbon, 40 ml methanol and 0.02 ml of saturated methanolic hydrogen chloride was heated at 50° under 50 psi hydrogen for 4 hours and allowed to cool to room temperature. The mixture was filtered and the methanol evaporated. The residue was dissolved in ether, washed with saturated sodium carbonate and saturated sodium chloride, and dried over potassium carbonate. Filtration followed by evaporation of the solvent provided an oil. The oxalate was recrystallized from ethanol to provide 0.42 g (45%) of 1-{N-{3-[2-(4-fluorophenyl)-1,3-dioxolan-2-yl]propyl}-N-methylaminoacetyl}-4-phenoxypiperidine oxalate.

Analysis: Calculated for $C_{28}H_{35}FN_2O_8$: 61.52%C, 6.45%H, 5.13%N. Found: 61.92%C, 6.39%H, 5.15%N.

EXAMPLE 18

1-{2-{N-{3-[2-(4-Fluorophenyl)-1,3-dioxolan-2-yl]propyl}-N-ethylamino}ethyl}-4-(3-chlorophenoxy)piperidine dihydrochloride A solution of 1-{2-{N-{3-[2-(4-fluorophenyl)-1,3-dioxolan-2-yl]propyl}-N-benzylamino}ethyl}-4-(3-chlorophenoxy)piperidine in 30 ml of methanol was made acidic (pH 6) by dropwise addition of methanolic hydrogen chloride. To the mixture was added 0.3 g of 5% palladium on carbon. The mixture was shaken at 50° C. under 50 psi hydrogen for 0.5 hour and allowed to cool to room temperature. The suspension was filtered and the methanol evaporated from the filtrate. The residual solid was shaken with 15% NaOH/ether, extracted twice with ether, washed with sodium chloride and dried over potassium carbonate. Filtration followed by evaporation of the solvent provided an oil. Addition of ethereal HCl to an ethereal solution of the product provided 0.54 g of the dihydrochloride. Recrystallization from ethanol provided 0.22 g of 1-{2-{N-{3-[2-(4-fluorophenyl)-1,3-dioxolan-2-yl]propyl}-N-ethylamino}ethyl}-4-(3-chlorophenoxy)piperidine dihydrochloride.

Analysis: Calculated for $C_{25}H_{32}ClFN_2O_3.2HCl$: 56.03%C, 6.39%H, 5.23%N. Found: 56.06%C, 6.53%H, 5.18%N.

EXAMPLE 19

1-{N-{3-[2-(4-Fluorophenyl)-1,3-dioxolan-2-yl]propyl}-N-methylaminoacetyl}-4-(4-fluorophenoxy)piperidine oxalate To a suspension of 9.16 g of sodium bicarbonate, 110 ml of dichloromethane and 4.23 ml (47.4 mmol) of bromoacetyl bromide cooled at 0° was added dropwise a solution of 8.68 g (44.5 mmol) of 4-(4-fluorophenoxy)piperidine (distilled at 92°-95°/0.2 mm Hg) in 110 ml of dichloromethane. The mixture was stirred 1 hour at 0° and 3 hours at room temperature. The mixture was washed with water and saturated sodium chloride, dried over potassium carbonate and filtered. Evaporation of the solvent provided 11.2 g of 1-(N-bromoacetyl)-4-(4-fluorophenoxy)piperidine.

To a suspension of 2-(3-[methylamino]propyl)-2-(4-fluorophenyl)-1,3-dioxolane (liberated from 7.50 g, 31.2 mmol, of the hydrochloride salt) in 125 ml of ethanol was added dropwise a solution of 11.0 g (34.8 mmol) of 1-(N-bromoacetyl)-4-(4-fluorophenoxy)piperidine in 125 ml of ethanol. The mixture was stirred at room temperature for 1 hour and at reflux for 1 hour and allowed to cool to room temperature. The mixture was washed with saturated sodium bicarbonate, saturated sodium chloride and dried over potassium carbonate. Filtration followed by evaporation of the solvent provided an oil (11.2 g).

The oil was dissolved in anhydrous ether and decanted. The decanted solution was evaporated to provide an oil which was dissolved in a minimum volume of ether. The material was placed on a column containing 250 g alumina and eluted with 500 ml ether. The yield of the oxalate was 7.26 g (41%). Recrystallization from ethanol provided analytically pure material.

Analysis: Calculated for $C_{26}H_{32}F_2N_2O_4.(CO_2H)_2$: 59.56%C, 6.07%H, 4.96%N. Found: 59.62%C, 6.05%H, 4.89%N.

EXAMPLE 20

1-{2-{N-{3-[2-(4-Fluorophenyl)-1,3-dioxolan-2-yl]propyl}-N-methylamino}-ethyl}-4-(4-fluorophenoxy)piperidine dihydrochloride To a suspension of 1.4 g (21.1 mmol) of lithium aluminum hydride (57% in oil; washed 3 times with hexane) in 50 ml of dry THF, cooled at 0°, was added dropwise a solution of 1-{N-{3-[2-(4-Fluorophenyl)-1,3-dioxolan-2-yl]propyl}-N-methylaminoacetyl}-4-(4-fluorophenoxy)piperidine (liberated from 5.94 g (10.5 mmol) of the oxalate) in 50 ml of dry THF. The mixture was allowed to warm to room temperature and was then heated at reflux for 16 hours under nitrogen, allowed to cool to room temperature and subsequently cooled in an ice bath. To the mixture were added dropwise, slowly, 0.7 ml of water, 0.7 ml of 15% NaOH and 2 ml of water. The mixture was filtered and washed with 100 ml of THF. The solvent was evaporated from the filtrate to provide an oil. The oil was dissolved in ether, washed with water and saturated sodium chloride and dried over potassium carbonate. Filtration followed by evaporation of the solvent provided an oil. The yield of the dihydrochloride was 3.83 g (68%). Recrystallization from ethanol provided analytically pure material.

Analysis: Calculated for $C_{26}H_{34}F_2N_2O_3.2HCl$: 58.53%C, 6.80%H, 5.25%N. Found: 58.36%C, 6.43%H, 5.19%N.

EXAMPLE 21

1-{2-{N-[4-(4-Fluorophenyl)-4-oxobutyl]-N-methylamino}ethyl}-4-(4-fluorophenyl)piperidine dihydrochloride A suspension of 11.4 g (21.4 mmol) of 1-{2-{N-{3-[2-(4-fluorophenyl)-1,3-dioxolan-2-yl]propyl}-N-methylamino}ethyl}-4-(4-fluorophenoxy)piperidine dihydrochloride, 260 ml of methanol and 130 ml of 3N HCl was heated at reflux for 3 hours under nitrogen. The mixture was allowed to cool to room temperature and the methanol evaporated. The mixture was made basic with saturated sodium carbonate, extracted twice with ether, washed with saturated sodium chloride and dried over potassium carbonate. Evaporation of the solvent provided an oil. The yield of the dihydrochloride was 8.38 g (79.9%). Recrystallization from ethanol/methanol provided analytically pure material.

Analysis: Calculated for $C_{24}H_{30}F_2N_2O_2.2HCl$: 58.90%C, 6.59%H, 5.72%N. Found: 58.95%C, 6.74%H, 5.63%N.

EXAMPLE 22

1-{N-{3-[2-(4-Fluorophenyl)-1,3-dioxolan-2-yl]propyl}-N-methylaminoacetyl}-4-(2-fluorophenoxy)piperidine oxalate To a stirred suspension of 310 ml of methylene chloride, 26.3 g of sodium bicarbonate and 12.1 ml (136 mmol) of bromoacetyl bromide, cooled at 0°, was added dropwise a solution of 4-(2-fluorophenoxy)piperidine (liberated from 29.6 g, 123 mmol, of the hydrochloride) in 310 ml of methylene chloride. The mixture was stirred 1 hour in an ice bath and 4 hours at room temperature. The mixture was washed with water, extracted twice with methylene chloride, washed with saturated sodium chloride and dried over potassium carbonate. Filtration followed by evaporation of the solvent provided 27.0 g of 1-(N-bromoacetyl)-4-(2-fluorophenoxy)piperidine as an oil.

To a suspension of 2-(3-[methylamino]propyl)-2-(4-fluorophenyl)-1,3-dioxolane (liberated from 20.9 g, 75.8 mmol, of the hydrochloride), 300 ml of ethanol and 26.5 g (192 mmol) of anhydrous potassium carbonate cooled in an ice bath was added dropwise a solution of 27.0 g (85.4 mmol) of crude 1-(N-bromoacetyl)-4-(2-fluorophenoxy)piperidine in 300 ml ethanol. The mixture was stirred at room temperature for 3 hours and at reflux for 1 hour and allowed to cool to room temperature. The mixture was washed with saturated sodium bicarbonate, saturated sodium chloride and dried over potassium carbonate. Filtration followed by evaporation of the solvent provided an oil. The oil was treated with anhydrous ether and decanted. Addition of an ethereal solution of oxalic acid to the decanted solution provided, after filtration and drying, 31.4 g (55.6 mmol, 75%) of 1-{N-{3-[2-(4-fluorophenyl)-1,3-dioxolan-2-yl]propyl}-N-methylaminoacetyl}-4-(2-fluorophenoxy)piperidine oxalate. Recrystallization from ethanol provided analytically pure material.

Analysis: Calculated for $C_{26}H_{32}N_2O_4 \cdot C_2H_2O_4$: 59.56%C, 6.07%H, 4.96%N. Found: 59.40%C, 6.18H, 4.67%N.

EXAMPLE 23

1-{2-{N-{3-[(4-Fluorophenyl)-1,3-dioxolan-2-yl]propyl}-N-methylamino}-ethyl}-4-(2-fluorophenoxy)piperidine dihydrochloride To a stirred suspension of 7.38 g (0.503 mol) of lithium aluminum hydride (50% in oil; washed 3 times with hexanes) in 250 ml of dry THF at 0° was added dropwise a solution of 1-{N-{3-[2-(4-fluorophenyl)-1,3-dioxolan-2-yl]propyl}-N-methylaminoacetyl}-4-(2-fluorophenoxy)piperidine (liberated from 28.6 g, 50.6 mmol, of the oxalate) in 250 ml of THF. The mixture was allowed to warm to room temperature and subsequently heated at reflux for 24 hours under nitrogen. The mixture was allowed to cool to room temperature and subsequently cooled in an ice bath. To the mixture were added dropwise, slowly, 4 ml water, 4 ml 15% sodium hydroxide and 12 ml water. The suspension was filtered and the residue washed with THF. Evaporation of the solvent provided an oil which was shaken with saturated sodium carbonate, extracted twice with ether, washed with saturated sodium chloride and dried over potassium carbonate. Filtration followed by evaporation of the solvent provided an oil. The yield of the dihydrochloride was 20.26 g (44.0 mmol, 87%).

Analysis: Calculated for $C_{26}H_{34}F_2N_2O_3 \cdot 2HCl$: 58.53%C, 6.80%H, 5.25%N. Found: 58.21%C, 6.72%H, 5.24%N.

EXAMPLE 24

1-{2-{N-[4-(4-Fluorophenyl)-4-oxobutyl]-N-methylamino}ethyl}-4-(2-fluorophenoxy)piperidine dihydrochloride A solution of 17.8 g (33.4 mol) of 1-{2-{N-{3-[(4-fluorophenyl)-1,3-dioxolan-2-yl]propyl}-N-methylamino}ethyl}-4-(2-fluorophenoxy)piperidine dihydrochloride, 260 ml methanol and 110 ml 3N HCl was heated at reflux for 3 hours under nitrogen and cooled to room temperature. The solution was neutralized with saturated sodium bicarbonate and the methanol evaporated. The residue was made basic with sodium carbonate, extracted twice with ether, washed with saturated sodium chloride and dried over potassium carbonate. Evaporation of the solvent provided an oil. The yield of the dihydrochloride was 14.9 g (30.4 mmol). Recrystallization from ethanol provided 12.25 g (75%) of the desired ketone.

Analysis: Calculated for $C_{24}H_{30}F_2N_2O_2 \cdot 2HCl$: 58.89%C, 6.59%H, 5.72%N. Found: 59.20%C, 6.82%H, 5.55%N.

EXAMPLE 25

1-{2-{N-{3-[2-(4-Fluorophenyl)-1,3-dioxolan-2-yl]propyl}-N-methylamino}ethyl}-4-(4-chlorophenoxy)piperidine dihydrochloride To a suspension of 4.68 g of lithium aluminum hydride (61.7 mmol, 50% in oil; washed 3 times with hexane) in 160 ml of THF was added dropwise a solution of 1-{N-{3-[2-(4-fluorophenyl)-1,3-dioxolan-2-yl]propyl}-N-methylaminoacetyl}-4-(4-chlorophenoxy)piperidine (liberated from 34.7 g, 0.105 mol, of the oxalate) in 160 ml of dry THF. The mixture was stirred at reflux for 16 hours, allowed to cool to room temperature and subsequently cooled in an ice bath. To the mixture were added slowly, dropwise, 3 ml of water, 3 ml of 15% NaOH and 9 of ml water. The mixture was filtered and the residue washed with THF. Evaporation of the solvent provided an oil. The oil was washed with water, dried over potassium carbonate and the solvent evaporated to provide an oil. The yield of the dihydrochloride was 11.98 g (63%).

Analysis: Calculated for $C_{26}H_{34}ClFN_2O_3 \cdot 2HCl$: 56.78%C, 6.60%H, 5.10%N. Found: 56.68%C, 6.47%H, 5.12%N.

EXAMPLE 26

1-{2-{N-[4-(4-Fluorophenyl)-4-oxobutyl]-N-methylamino}ethyl}-4-(4-chlorophenoxy)piperidine dihydrochloride A solution of 8.94 g (17.7 mmol) of 1-{2-{N-{3-[2-(4-fluorophenyl)-1,3-dioxolan-2-yl]propyl}-N-methylamino}ethyl}-4-(4-chlorophenoxy)piperidine dihydrochloride, 135 ml of methanol, and 55 ml of 3N HCl was heated at reflux for 3 hours under nitrogen. The mixture was allowed to cool to room temperature, poured into saturated sodium carbonate, extracted twice with ether and dried over potassium carbonate. Filtration followed by evaporation of the solvent provided an oil. The yield of a crude dihydrochloride was 6.71 g (81%). Recrystallization from ethanol provided 2.37 g (28%) of the desired ketone.

Analysis: Calculated for $C_{24}H_{30}ClFN_2O_2 \cdot 2HCl$: 56.98%C, 6.38%H, 5.54%N. Found: 57.24%C, 6.35%H, 5.54%N.

EXAMPLE 27

1-{N-{3-[2-(4-Fluorophenyl)-1,3-dioxolan-2-yl]propyl}-N-methylaminoacetyl}-4-(4-chlorophenoxy)piperidine oxalate To an ice cold suspension of 41.4 g (0.493 mol) of sodium bicarbonate, 500 ml of methylene chloride and 19.1 ml (44.3 g, 0.219 mol) of bromoacetylbromide was added dropwise a solution of 4-(4-chlorophenoxy)piperidine which had been prepared from 50 g (0.201 mol) of the hydrochloride salt and 15% sodium hydroxide/methylene chloride. The mixture was stirred 1 hour at 0° and 3 hours at room temperature. The mixture was washed with water, saturated sodium chloride and dried over potassium carbonate. Filtration followed by evaporation of the solvent provided 59.0 g of 1-(N-bromoacetyl)-4-(4-chlorophenoxy)-piperidine as an oil.

To a stirred suspension of 2-(3-[methylamino]propyl)-2-(4-fluorophenyl)-1,3-dioxolane hydrochloride (liberated from 34.7 g, 0.105 mol, of the oxalate), 420 ml of ethanol and 37.1 g (0.268 mol) of potassium carbonate at 0° was added dropwise a solution of 40.0 g (0.120 mol)

of crude 1-(N-bromoacetyl)-4-(4-chlorophenoxy)piperidine in 420 ml ethanol. The mixture was stirred 1 hour at 0° and overnight at room temperature. The mixture was heated at reflux for 1 hour, allowed to cool to room temperature, poured into saturated sodium carbonate, extracted twice with ether, washed with saturated sodium chloride and dried over potassium carbonate. Evaporation of the solvent provided an oil. The oil was dissolved in anhydrous ether and the solution decanted from a gum. The ether solution was allowed to stand for 72 hours and again decanted. The yield of 1-{N-{3-[2-(4-fluorophenyl)-1,3-dioxolan-2-yl]propyl}-N-methylaminoacetyl}-4-(4-chlorophenoxy)piperidine was 34.3 g (57.3 mmol, 47.8%).

Analysis: Calculated for $C_{26}H_{19}ClFN_2O_4.(CO_2H)_2.H_2O$: 56.14%C, 6.06%H, 4.68%N. Found: 56.03%C, 5.92%H, 4.44%N.

EXAMPLE 28

1-{2-{N-{[3-(4-Fluorophenyl)-1,3-dioxolan-2-yl]propyl}-N-methylamino}ethyl}-4-(4-methylphenoxy)piperidine dihydrochloride To a stirred suspension of 1.61 g (24.3 mmol) of lithium aluminum hydride (57% in oil; washed 3 times with hexane) in 60 ml of dry THF was added dropwise a solution of 1-{N-{3-[2-(4-fluorophenyl)-1,3-dioxolan-2-yl]propyl}-N-methylaminoacetyl}-4-(4-methylphenoxy)piperidine (liberated from 5.68 g (10.1 mmol) of the oxalate) in 60 ml of dry THF. The mixture was stirred at reflux under nitrogen for 16 hours. The mixture was allowed to cool to room temperature and subsequently cooled in an ice bath. To the mixture were added, slowly, dropwise, 1 ml of water, 1 ml of 15% sodium hydroxide and 3 ml of water. The mixture was filtered and the residue washed with THF. The filtrate was concentrated to an oil. The oil was dissolved in ether, washed with water and saturated NaCl, dried over potassium carbonate, filtered and the solvent evaporated to provide an oil. The yield of 1-{2-{N-{[3-(4-fluorophenyl)-1,3-dioxolan-2-yl]propyl}-N-methylamino}ethyl}-4-(4-methylphenoxy)piperidine was 4.33 g (8.18 mmol, 81%). The dihydrochloride, after recrystallization from ethanol, melted at 245°–256°.

Analysis: Calculated for $C_{27}H_{37}FN_2O_3.2HCl$: 61.24%C, 7.42%H, 5.29%N. Found: 61.64%C, 7.38%H, 5.48%N.

EXAMPLE 29

1-{N-{3-[2-(4-Fluorophenyl)-1,3-dioxolan-2-yl]propyl}-N-methylaminoacetyl}-4-(4-methylphenoxy)piperidine oxalate To a suspension of 16.7 g (0.121 mol) of potassium carbonate, 190 ml of ethanol, and 47.4 mmol of 2-(3-[methylamino]propyl)-2-(4-fluorophenyl)-1,3-dioxolane hydrochloride, (liberated from 15.6 g of the oxalate) at 0° was added dropwise a solution of 18.0 g (57.7 mmol) of 1-(N-bromoacetyl)-4-(4-methylphenoxy)piperidine (prepared from 4-(4-methylphenoxy)piperidine) in 190 ml of ethanol. The mixture was allowed to warm to room temperature and stirred for 16 hours. The mixture was stirred at reflux for 1 hour and allowed to cool to room temperature. The mixture was diluted with water, extracted twice with ether and washed with saturated sodium chloride. The solution was dried over potassium carbonate and filtered. Evaporation of the solvent provided an oil. The yield of the oxalate was 17.6 g. The free base was liberated (methylene chloride/saturated sodium carbonate) and placed on a column packed with 900 g of alumina (80–200 mesh). The column was eluted three times using 1 liter aliquots of ether. The desired amide was contained in fractions two and three. Evaporation of the solvent provided an oil. The oxalate was recrystallized from ethanol to provide 4.99 g (8.90 mol, 18.8%) of 1-{N-{3-[2-(4-fluorophenyl)-1,3-dioxolan-2-yl]propyl}-N-methylaminoacetyl}-4-(4-methylphenoxy)piperidine oxlate, m.p. 162–165.

Analysis: Calculated for $C_{27}H_{35}FN_2O_4.C_2H_2O_4$: 62.13%C, 6.65%H, 5.00%N. Found: 61.80%C, 6.58%H, 4.76%N.

EXAMPLE 30

4-(4-Acetylphenoxy)piperidine oxalate

To a stirred solution of dimsyl sodium, prepared from 43.2 g of NaH (0.90 mol; 50% in oil, washed 3 times with hexane) and 1200 ml of DMSO was added in aliquots, 100 g (0.989 mol) of 4-hydroxypiperidine such that the temperature remained below 23° (using an ice bath). To the mixture was then added dropwise 120 ml (0.99 mol) of p-fluoroacetophenone. The mixture was then stirred at room temperature overnight, poured into water, extracted twice with ether, washed with saturated sodium chloride and dried over potassium carbonate. Filtration followed by evaporation of the solvent provided an oil. The oil was filtered through 500 g of alumina and eluted 2×500 ml of 5% methanol/ether and 2×500 ml of 10% methanol/ether. The material was contained in fractions 2–4. Evaporation of the solvent provided an oil. The yield of the oxalate was 51.2 g (0.165 mol, 18.4%). Recrystallization from methanol provided analytically pure material, m.p. 183–187.

Analysis: Calculated for $C_{13}H_{17}NO_2.C_2H_2O_4$: 58.24%C, 6.19%H, 4.53%N. Found: 58.70%C, 6.22%H, 4.36%N.

EXAMPLE 31

1-{N-{3-[2-(4-Fluorophenyl)-1,3-dioxolan-2-yl]propyl}-N-methylaminoacetyl}-4-(4-acetylphenoxy)piperidine oxalate To a stirred solution of 10.4 g (0.124 mol) of sodium bicarbonate, 125 ml of dichloromethane (dried over magnesium sulfate) and 4.76 ml (54.7 mmol) of bromoacetylbromide maintained in an ice bath and under nitrogen was added dropwise a solution of 4-(4-acetylphenoxy)piperidine (liberated from 15.0 g, 48.5 mmol, of the oxalate) in 125 ml of dry dichloromethane. The mixture was stirred at 0° for 45 minutes and allowed to warm to room temperature over 45 minutes. The mixture was poured into ice water, extracted twice with dichloromethane and dried over potassium carbonate. Filtration followed by evaporation of the solvent provided 15.7 g (46.1 mmol) of 1-(N-bromoacetyl)-4-(4-acetylphenoxy)piperidine, as an oil.

To a stirred suspension of 41.0 mmol of 2-(3-[methylamino]-propyl)-2-(p-fluorophenyl)-1,3-dioxolane (liberated from 11.3 g of the hydrochloride), 14.3 g (0.104 mol) of potassium carbonate and 160 ml of ethanol, cooled in an ice bath was added dropwise a solution of 15.7 g (46.1 mmol) of 1-(N-bromoacetyl)-4-(4-acetylphenoxy)piperidine in 160 ml of ethanol. Following the addition, the mixture was allowed to warm to room temperature, stirred for 2 hours and subsequently at reflux for 1 hour. The mixture was poured into cold saturated sodium carbonate, extracted twice with ether, washed with saturated sodium chloride, dried over potassium carbonate, filtered and the solvent evaporated to provide 11.7 g of an oil. The oil was dissolved in a minimum volume of ether, filtered through 150 g of alumina and eluted with 450 ml of ether. Evaporation of the solvent provided an oil. The oxalate of 1-{N-{3-[2-(4-fluorophenyl)-1,3-dioxolan-2-yl]propyl}-N-methylaminoacetyl}-4-(4-acetylphenoxy)piperidine was recrystallized from ethanol to provide 3.54 g (10.4 mol, 25.4%), m.p. 159°–167°.

Analysis: Calculated for $C_{28}H_{35}N_2O_5C_2H_2O_4$: 61.21%C, 6.34%H, 4.76%N. Found: 61.16%C, 6.20%H, 4.60%N.

EXAMPLE 32

4-(4-Ethylphenoxy)piperidine

A solution of 4-(4-acetylphenoxy)piperidine (liberated from 15.0 g, 48.5 mmol, of the oxalate), 7.45 g of potassium hydroxide, 5.39 ml of 85% hydrazine hydrate and 54 ml of triethyleneglycol was stirred at reflux for 1 hour. The mixture was then cooled to room temperature and the flask fitted with a distillation apparatus. The temperature was then raised to 190°–195° and water removed by distillation. The mixture was stirred at 190°–195° for 3 hours and the mixture allowed to cool to room temperature. The mixture was diluted with water, extracted twice with ether and with 1N HCl, made basic with saturated sodium carbonate, extracted with ether and dried over potassium carbonate. Filtration followed by evaporation of the solvent provided an oil. Kugelrohr distillation at 114°–116°/1 mm provided 3.84 g (18.7 mmol, 38.6%) of 4-(4-ethylphenoxy)piperidine, m.p. 37–41.

Analysis: Calculated for $C_{13}H_{19}NO$: 76.05%C, 9.33%H, 6.82%N. Found: 75.92%C, 9.32%H, 6.69%N.

EXAMPLE 33

1-{N-{3-[2-(4-Fluorophenyl)-1,3-dioxolan-2-yl]propyl}-N-methylaminoacetyl}-4-(4-ethylphenoxy)-piperidine oxalate To a stirred suspension of 6.03 ml (69.3 mmol) of bromoacetyl bromide, 13.0 g (155 mmol) of sodium bicarbonate and 160 ml of dry dichloromethane in an ice bath was added dropwise a solution of 13.0 g (63.4 mmol) of 4-(4-ethylphenoxy)piperidine in 140 ml of dry dichloromethane. The mixture was stirred 1 hour at 0° and 45 minutes at room temperature. The mixture was subsequently poured into water, extracted twice with dichloromethane, washed with saturated sodium chloride and dried over potassium carbonate. Filtration followed by evaporation of the solvent provided 20.0 g (61.3 mmol) of 1-(2-bromoacetyl)-4-(4-ethylphenoxy)-piperidine as an oil.

To a stirred suspension of 215 ml of ethanol, 19.0 g (138 mmol) of potassium carbonate, and 2-(3-[methylamino]propyl)-2-(4-fluorophenyl)-1,3-dioxolane (liberated from 15.0 g, 54.4 mmol, of the hydrochloride) at 0° was added dropwise a solution of 20.0 g (61.3 mmol) of 1-(2-bromoacetyl)-4-(4-ethylphenoxy)piperidine in 215 ml of ethanol. Following addition the mixture was allowed to warm to room temperature, stirred for 2 hours and subsequently at reflux for 1 hour. The mixture was allowed to cool to room temperature, poured into water/ice/sodium carbonate, extracted twice with ether, washed with saturated sodium chloride and dried over potassium carbonate. Filtration followed by evaporation of the solvent provided 15.1 g (30.9 mmol, 50.5%) of an oil. The material was filtered through 250 g of alumina using 750 ml of ether. Evaporation of the solvent provided an oil, the oxalate of which was recrystallized from ethanol to provide 5.82 g (10.1 mmol, 18.6%) of analytically pure 1-{N-{3-[2-(4-fluorophenyl)-1,3-dioxolan-2-yl]propyl}-N-methylaminoacetyl}-4-(4-ethylphenoxy)piperidine oxalate, m.p. 165°–175°.

Analysis: Calculated for $C_{28}H_{37}FN_2O_4.C_2H_2O_4$: 62.70%C, 6.84%H, 4.88%N. Found: 62.85%C, 6.87%H, 4.73%N.

We claim:

1. A compound of the formula

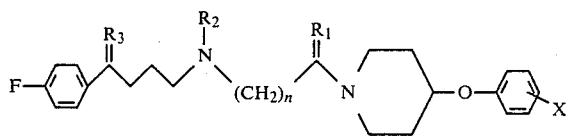

where X is hydrogen, loweralkyl, $CF_3$, acetyl or halogen; n is 1 or 2; $R_1$ is $H_2$ or oxygen; $R_2$ is H, loweralkyl or benzyl; and $R_3$ is oxygen or $-OCH_2CH_2O-$, or a pharmaceutically acceptable acid addition salt thereof.

2. The compound as defined in claim 1, wherein n is 1.

3. The compound as defined in claim 2, wherein X is hydrogen.

4. The compound as defined in claim 2, wherein X is loweralkyl.

5. The compound as defined in claim 2, wherein X is $CF_3$.

6. The compound as defined in claim 2, wherein X is acetyl.

7. The compound as defined in claim 2, wherein X is halogen.

8. The compound as defined in claim 7, wherein X is fluorine.

9. The compound as defined in claim 7, wherein X is chlorine.

10. The compound as defined in claim 2, wherein $R_1$ is oxygen.

11. The compound as defined in claim 3, wherein $R_1$ is oxygen.

12. The compound as defined in claim 4, wherein $R_1$ is oxygen.

13. The compound as defined in claim 5, wherein $R_1$ is oxygen.

14. The compound as defined in claim 6, wherein $R_1$ is oxygen.

15. The compound as defined in claim 7, wherein $R_1$ is oxygen.

16. The compound as defined in claim 8, wherein $R_1$ is oxygen.

17. The compound as defined in claim 9, wherein $R_1$ is oxygen.

18. The compound as defined in claim 2, wherein $R_1$ is $H_2$.

19. The compound as defined in claim 3, wherein $R_1$ is $H_2$.

20. The compound as defined in claim 4, wherein $R_1$ is $H_2$.

21. The compound as defined in claim 5, wherein $R_1$ is $H_2$.

22. The compound as defined in claim 6, wherein $R_1$ is $H_2$.

23. The compound as defined in claim 7, wherein $R_1$ is $H_2$.

24. The compound as defined in claim 8, wherein $R_1$ is $H_2$.

25. The compound as defined in claim 9, wherein $R_1$ ia $H_2$.

26. The compound as defined in claim 2, wherein $R_2$ is hydrogen.

27. The compound as defined in claim 3, wherein $R_2$ is hydrogen.

28. The compound as defined in claim 4, wherein $R_2$ is hydrogen.

29. The compound as defined in claim 5, wherein $R_2$ is hydrogen.

30. The compound as defined in claim 6, wherein $R_2$ is hydrogen.

31. The compound as defined in claim 7, wherein $R_2$ is hydrogen.

32. The compound as defined in claim 8, wherein $R_2$ is hydrogen.

33. The compound as defined in claim 9, wherein $R_2$ is hydrogen.

34. The compound as defined in claim 2, wherein $R_2$ is loweralkyl.

35. The compound as defined in claim 3, wherein $R_2$ is loweralkyl.

36. The compound as defined in claim 4, wherein $R_2$ is loweralkyl.

37. The compound as defined in claim 5, wherein $R_2$ is loweralkyl.

38. The compound as defined in claim 6, wherein $R_2$ is loweralkyl.

39. The compound as defined in claim 7, wherein $R_2$ is loweralkyl.

40. The compound as defined in claim 8, wherein $R_2$ is loweralkyl.

41. The compound as defined in claim 9, wherein $R_2$ is loweralkyl.

42. The compound as defined in claim 2, wherein $R_2$ is benzyl.

43. The compound as defined in claim 3, wherein $R_2$ is benzyl.

44. The compound as defined in claim 4, wherein $R_2$ is benzyl.

45. The compound as defined in claim 5, wherein $R_2$ is benzyl.

46. The compound as defined in claim 6, wherein $R_2$ is benzyl.

47. The compound as defined in claim 7, wherein $R_2$ is benzyl.

48. The compound as defined in claim 8, wherein $R_2$ is benzyl.

49. The compound as defined in claim 9, wherein $R_2$ is benzyl.

50. The compound as defined in claim 2, wherein $R_3$ is oxygen.

51. The compound as defined in claim 3, wherein $R_3$ is oxygen.

52. The compound as defined in claim 4, wherein $R_3$ is oxygen.

53. The compound as defined in claim 5, wherein $R_3$ is oxygen.

54. The compound as defined in claim 6, wherein $R_3$ is oxygen.

55. The compound as defined in claim 7, wherein $R_3$ is oxygen.

56. The compound as defined in claim 8, wherein $R_3$ is oxygen.

57. The compound as defined in claim 9, wherein $R_3$ is oxygen.

58. The compound as defined in claim 2, wherein $R_3$ is $-OCH_2CH_2O-$.

59. The compound as defined in claim 3, wherein $R_3$ is $-OCH_2CH_2O-$.

60. The compound as defined in claim 4, wherein $R_3$ is $-OCH_2CH_2O-$.

61. The compound as defined in claim 5, wherein $R_3$ is $-OCH_2CH_2O-$.

62. The compound as defined in claim 6, wherein $R_3$ is $-OCH_2CH_2O-$.

63. The compound as defined in claim 7, wherein $R_3$ is $-OCH_2CH_2O-$.

64. The compound as defined in claim 8, wherein $R_3$ is $-OCH_2CH_2O-$.

65. The compound as defined in claim 9, wherein $R_3$ is $-OCH_2CH_2O-$.

66. The compound as defined in claim 11, which is 1-{N-{3-[2-(4-fluorophenyl)-1,3-dioxolan-2-yl]propyl}-N-methylaminoacetyl}-4-phenoxypiperidine, or a pharmaceutically acceptable acid addition salt thereof.

67. The compound as defined in claim 12, which is 1-{N-{3-[2-(4-fluorophenyl)-1,3-dioxolan-2-yl]propyl}-N-methylaminoacetyl}-4-(4-methylphenoxy)piperidine or a pharmaceutically acceptable acid addition salt thereof.

68. The compound as defined in claim 12, which is 1-{N-{3-[2-(4-fluorophenyl)-1,3-dioxolan-2-yl]propyl}-N-methylaminoacetyl}-4-(4-ethylphenoxy)piperidine oxalate or a pharmaceutically acceptable acid addition salt thereof.

69. The compound as defined in claim 13, which is 1-{2-{N-{3-[2-(4-fluorophenyl)-1,3-dioxolan-2-yl]propyl}-N-methylamino}acetyl}-4-trifluoromethylphenoxy)piperidine oxalateor a pharmaceutically acceptable acid addition salt thereof.

70. The compound as defined in claim 14, which is 1-{N-{3-[2-(4-fluorophenyl)-1,3-dioxolan-2-yl]propyl}-N-methylaminoacetyl}-4-(4-acetylphenoxy)piperidine or a pharmaceutically acceptable acid addition salt thereof.

71. The compound as defined in claim 16, which is 1-{N-{3-[2-(4-fluorophenyl)-1,3-dioxolan-2-yl]propyl}-N-methylaminoacetyl}-4-(2-fluorophenoxy)piperidine or a pharmaceutically acceptable acid addition salt thereof.

72. The compound as defined in claim 17, which is 1-{2-{N-{3-[2-(4-Fluorophenyl)-1,3-dioxolan-2-yl]propyl}-N-methylamino}ethyl}-4-(3-chlorophenoxy)piperidine dihydrochloride or a pharmaceutically acceptable acid addition salt thereof.

73. The compound as defined in claim 17, which is 1-{N-{3-[2-(4-fluorophenyl)-1,3-dioxolan-2-yl]propyl}-N-methylaminoacetyl}-4-(4-chlorophenoxy)piperdine or a pharmaceutically acceptable acid addition salt thereof.

74. The compound as defined in claim 19, which is 1-{2-{N-{3-[2-(4-fluorophenyl)-1,3-dioxolan-2-yl]propyl}-N-methylamino}ethyl}-4-phenoxypiperidine dihydrochloride or a pharmaceutically acceptable acid addition salt thereof.

75. The compound as defined in claim 19, which is 1-{2-{N-[4-(4-fluorophenyl)-4-oxobutyl]-N-methylamino}ethyl}-4-phenoxypiperidine dihydrochloride or a pharmaceutically acceptable acid addition salt thereof.

76. The compound as defined in claim 20, which is 1-{2-{N-{[3-(4-fluorophenyl)-1,3-dioxolan-2-yl]propyl}-N-methylamino}ethyl}-4-(4-methylphenoxy)piperidine dihydrochloride or a pharmaceutically acceptable acid addition salt thereof.

77. The compound as defined in claim 21, which is 1-{2-{N-[4-(4-fluorophenyl)-4-oxobutyl]-N-methylamino}ethyl}-4-(4-trifluoromethylphenoxy)piperidine or a pharmaceutically acceptable acid addition salt thereof.

78. The compound as defined in claim 24, which is 1-{N-{3-[2-(4-fluorophenyl)-1,3-dioxolan-2-yl]propyl}-N-methylaminoacetyl}-4-(4-fluorophenoxy)piperidine or a pharmaceutically acceptable acid addition salt thereof.

79. The compound as defined in claim 24, which is 1-{2-{N-{3-[2-(4-fluorophenyl)-1,3-dioxolan-2-yl]propyl}-N-methylamino}ethyl}-4-(4-fluorophenoxy)piperidine or a pharmaceutically acceptable acid addition salt thereof.

80. The compound as defined in claim 24, which is 1-{2-{N-[4-(4-fluorophenyl)-4-oxobutyl]-N-methylamino}ethyl}-4-(4-fluorophenoxy)piperidine or a pharmaceutically acceptable acid addition salt thereof.

81. The compound as defined in claim 24, which is 1-{2-{N-{3-[(4-fluorophenyl)-1,3-dioxolan-2-yl]propyl}-N-methylamino}-ethyl}-4-(2-fluorophenoxy)piperidine or a pharmaceutically acceptable acid addition salt thereof.

82. The compound as defined in claim 24, which is 1-{2-{N-[4-(4-fluorophenyl)-4-oxobutyl]-N-methylamino}ethyl}-4-(2-fluorophenoxy)piperidine or a pharmaceutically acceptable acid addition salt thereof.

83. The compound as defined in claim 25, which is 1-{N-[3'-2-(4-fluorophenyl)-1,3-dioxolan-2-yl]propyl-N-methylaminoethyl}-4-(3-chlorophenoxy)piperidine or a pharmaceutically acceptable acid addition salt thereof.

84. The compound as defined in claim 25, which is 1-{2-{N-[4-(4-fluorophenyl)-4-oxobutyl]-N-methylamino}ethyl}-4-(3-chlorophenoxy)piperidine dihydrochloride or a pharmaceutically acceptable acid addition salt thereof.

85. The compound as defined in claim 25, which is 1-{2-{N-{3-[2-(4-fluorophenyl)-1,3-dioxolan-2-yl]propyl}-N-ethylamino}ethyl}-4-(3-chlorophenoxy)piperidine dihydrochloride or a pharmaceutically acceptable acid addition salt thereof.

86. The compound as defined in claim 25, which is 1-{2-{N-[4-(4-fluorophenyl)-4-oxobutyl]-N-ethylamino}ethyl}-4-(3-chlorophenoxy)piperidine dihydrochloride or a pharmaceutically acceptable acid addition salt thereof.

87. The compound as defined in claim 25, which is 1-{2-{N-{3-[2-(4-fluorophenyl)-1,3-dioxolan-2-yl]propyl}-N-benzylamino}ethyl}-4-(3-chlorophenoxy)piperidine or a pharmaceutically acceptable acid addition salt thereof.

88. The compound as defined in claim 25, which is 1-{2-{N-{3-[2-(4-fluorophenyl)-1,3-dioxolan-2-yl]propyl}-N-ethylamino}ethyl}-4-(3-chlorophenoxy)piperidine dihydrochloride or a pharmaceutically acceptable acid addition salt thereof.

89. The compound as defined in claim 25, which is 1-{2-{N-{3-[2-(4-fluorophenyl)-1,3-dioxolan-2-yl]propyl}-N-methylamino}ethyl}-4-(4-chlorophenoxy)piperidine or a pharmaceutically acceptable acid addition salt thereof.

90. The compound as defined in claim 25, which is 1-{2-{N-[4-(4-fluorophenyl)-4-oxobutyl]-N-methylamino}ethyl}-4-(4-chlorophenoxy)piperidine or a pharmaceutically acceptable acid addition salt thereof.

91. The compound as defined in claim 1, wherein n is 2.

92. The compound as defined in claim 91, wherein X is hydrogen.

93. The compound as defined in claim 91, wherein X is loweralkyl.

94. The compound as defined in claim 91, wherein X is $CF_3$.

95. The compound as defined in claim 91, wherein X is halogen.

96. The compound as defined in claim 91, wherein X is fluorine.

97. The compound as defined in claim 91, wherein X is chlorine.

98. The compound as defined in claim 91, wherein $R_1$ is $H_2$.

99. The compound as defined in claim 92, wherein $R_1$ is $H_2$.

100. The compound as defined in claim 93, wherein $R_1$ is $H_2$.

101. The compound as defined in claim 94, wherein $R_1$ is $H_2$.

102. The compound as defined in claim 95, wherein $R_1$ is $H_2$.

103. The compound as defined in claim 96, wherein $R_1$ is $H_2$.

104. The compound as defined in claim 97, wherein $R_1$ is $H_2$.

105. The compound as defined in claim 91, wherein $R_2$ is loweralkyl.

106. The compound as defined in claim 92, wherein $R_2$ is loweralkyl.

107. The compound as defined in claim 93, wherein $R_2$ is loweralkyl.

108. The compound as defined in claim 94, wherein $R_2$ is loweralkyl.

109. The compound as defined in claim 95, wherein $R_2$ is loweralkyl.

110. The compound as defined in claim 96, wherein $R_2$ is loweralkyl.

111. The compound as defined in claim 97, wherein $R_2$ is loweralkyl.

112. The compound as defined in claim 104, which is 1-{3-{N-{3-[2-(4-fluorophenyl)-1,3-dioxolan-2-yl]propyl}-N-methyl-amino}propyl}-4-(3-chlorophenoxy)piperidine dihydrochloride or a pharmaceutically acceptable acid addition salt thereof.

113. The compound as defined in claim 104, which is 1-{3-{N-[4-(4-fluorophenyl)-4-oxobutyl]-N-methylamino}propyl}-4-(3-chlorophenoxy)piperidine or a pharmaceutically acceptable acid addition salt thereof.

114. An analgesic composition which comprises an effective pain alleviating amount of a compound of the formula

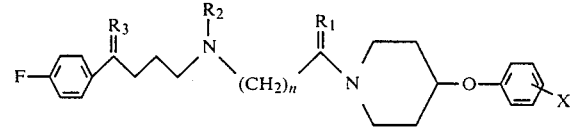

where X is hydrogen, loweralkyl, $CF_3$, acetyl or halogen; n is 1 or 2; $R_1$ is $H_2$ or oxygen; $R_2$ is H, loweralkyl or benzyl; and $R_3$ is oxygen or —$OCH_2CH_2O$— or a pharmaceutically acceptable acid addition salt thereof.

* * * * *

UNITED STATES PATENT AND TRADEMARK OFFICE
CERTIFICATE OF CORRECTION

PATENT NO. : 4,518,713
DATED : May 21, 1985
INVENTOR(S) : Raymond W. Kosley, Jr., et al.

It is certified that error appears in the above-identified patent and that said Letters Patent is hereby corrected as shown below:

Column 3, Line 31: "is" should read -- or --.

Column 7, Line 20: "3 chlorophenoxy" should read -- 3-chlorophenoxy --.

Column 8, Line 64 (which looks like line 66):
"4 Fluorophenyl" should read -- 4-Fluorophenyl --.

Column 9, line 50: "55" should read -- { --.

Column 9, line 62: "55" should read -- { --.

Signed and Sealed this

Tenth Day of September 1985

[SEAL]

Attest:

DONALD J. QUIGG

Attesting Officer   Acting Commissioner of Patents and Trademarks - Designate